United States Patent
Wendlinger

(10) Patent No.: US 9,783,471 B2
(45) Date of Patent: Oct. 10, 2017

(54) METHOD OF FLUORINATION IN THE GASEOUS PHASE

(71) Applicant: Arkema France, Colombes (FR)

(72) Inventor: Laurent Wendlinger, Soucieu en Jarrest (FR)

(73) Assignee: Arkema France, Colombes (FR)

(*) Notice: Subject to any disclaimer, the term of this patent is extended or adjusted under 35 U.S.C. 154(b) by 0 days.

(21) Appl. No.: 15/023,475

(22) PCT Filed: Sep. 17, 2014

(86) PCT No.: PCT/FR2014/052309
§ 371 (c)(1),
(2) Date: Mar. 21, 2016

(87) PCT Pub. No.: WO2015/044558
PCT Pub. Date: Apr. 2, 2015

(65) Prior Publication Data
US 2016/0207855 A1    Jul. 21, 2016

(30) Foreign Application Priority Data

Sep. 24, 2013   (FR) ..................... 13 59143

(51) Int. Cl.
*C07C 17/20* (2006.01)
*C07C 17/25* (2006.01)
*C07C 21/18* (2006.01)

(52) U.S. Cl.
CPC ............ *C07C 17/20* (2013.01); *C07C 17/206* (2013.01); *C07C 17/25* (2013.01)

(58) Field of Classification Search
CPC ....... C07C 17/20; C07C 17/206; C07C 17/25; C07C 21/18
See application file for complete search history.

(56) References Cited

U.S. PATENT DOCUMENTS

2006/0106263 A1*  5/2006  Miller .............. C01B 7/196
                                                    570/155
2011/0015452 A1*  1/2011  Devic .............. B01J 23/866
                                                    570/140

FOREIGN PATENT DOCUMENTS

WO   WO 2008/054781 A1   5/2008
WO   WO 2008/060616 A2   5/2008
WO   WO 2009/158321 A1   12/2009
WO   WO 2012/098420 A1   7/2012

OTHER PUBLICATIONS

International Search Report dated Dec. 5, 2014 for PCT/FR2014/052309.

* cited by examiner

*Primary Examiner* — Jafar Parsa
(74) *Attorney, Agent, or Firm* — Brinks Gilson & Lione

(57) ABSTRACT

The present invention concerns a method of producing at least one compound of formula (II): $CF_3-CX(Z)_n-CHX(Z)_n$ in which X represents, independently, a hydrogen, fluorine or chlorine atom, Z represents, independently, a hydrogen or fluorine atom, and n=0 or 1, from at least one compound of formula (I): $CX(Y)_2-CX(Y)_m-CH_mXY$ in which X and Y represent, independently, a hydrogen, fluorine or chlorine atom and m=0 or 1. The method comprises at least one step during which at least one compound of formula (I) reacts with HF in the gaseous phase in the presence of a fluorination catalyst in order to give at least one compound of formula (II), characterized in that the catalyst is made from chromium oxyfluoride containing at least nickel as the co-metal and at least one rare earth metal.

15 Claims, No Drawings

METHOD OF FLUORINATION IN THE GASEOUS PHASE

This application is a U.S. National Stage application of International Application No. PCT/FR2014/052309, filed Sep. 17, 2014, which claims the benefit of French Application No. 13.59143, filed Sep. 24, 2013.

The present invention relates to a process for gas-phase fluorination in the presence of a catalyst.

On account of its low Global Warming Potential, 2,3,3,3-tetrafluoropropene (HFO-1234yf) is considered as a potential candidate for replacing HFC-134a in motor vehicle air-conditioning.

2,3,3,3-Tetrafluoropropene may be obtained from 1,2,3,3-pentafluoropropene (HFO-1225ye) by reacting HFO-1225ye with hydrogen in the presence of a hydrogenation catalyst to give 1,1,1,2,3-pentafluoropropane (HFC-245eb); the HFC-245eb thus formed is then subjected to a dehydrofluorination step in the presence of potassium hydroxide (Knunyants et al., Journal of Academy of Sciences of the USSR, pages 1312-1317, August, 1960).

2,3,3,3-Tetrafluoropropene may also be obtained by reacting 2-chloro-3,3,3-trifluoropropene (HCFO-1233xf) with HF in the presence of a catalyst to give, in a first stage, 2-chloro-2,3,3,3-tetrafluoropropane (HCFC 244bb), and the HCFC-244bb is then dehydrochlorinated on a second catalyst (WO 2007/079431).

2,3,3,3-Tetrafluoropropene may also be obtained from pentachloropropanes or tetrachloropropenes by proceeding via 2-chloro-3,3,3-trifluoropropene as intermediate.

Certain metal oxides are used as catalyst or catalytic precursor in the manufacture of saturated and unsaturated hydrofluorocarbons. Thus, chromium oxide, in particular chromium(III) in the presence of HF at high temperature, gives a mixture of chromium fluoride and chromium oxyfluoride, which is very active in reactions for the substitution of at least one chlorine atom (C—Cl) with a fluorine atom (C—F). This substitution is a key step in the majority of the hydrochlorocarbon fluorination processes.

Catalysts based on chromium oxide in gas-phase fluorination reactions may be prepared by reduction of chromium (VI) trioxides or by precipitation of a chromium(III) salt with bases.

Besides chromium oxide and/or chromium oxyfluoride, the fluorination catalysts may contain at least one other metal such as zinc, nickel, magnesium and cobalt.

The fluorination catalysts may also be supported.

WO 2010/123154 describes a process for manufacturing HFO-1234yf by reacting HCFO-1233xf with HF in the presence of oxygen using an optionally fluorinated chromium oxide catalyst of formula $CrO_m$, with $1.5<m<3$. Said document teaches that, in order to obtain good selectivity toward HFO-1234yf, the reaction temperature must be between 330 and 380° C. at a pressure of 0.08 to 0.2 MPa with a mole ratio of oxygen relative to the HCFO-1233xf of between 0.1 and 1 and a mole ratio of HF relative to the HCFO-1233xf of between 4 and 30.

WO 2010/123154 is interested only in the selectivity toward HFO-1234yf for a very short reaction time (45 hours maximum). Thus, the conversion is only 6.2% in Example 3 after 45 hours of reaction.

Now, in order for a process to be industrially viable, not only must the selectivity be high, but also the conversion. In addition, the performance qualities must be virtually constant over time.

The Applicant has now developed a process for manufacturing at least one compound of formula (II): $CF_3$—$CX(Z)_n$—$CHX(Z)_n$ in which X independently represents a hydrogen, fluorine or chlorine atom, Z independently represents a hydrogen or fluorine atom and n=0 or 1, which may be performed industrially and which does not have the drawbacks of the prior art. More precisely, the present invention provides a process for manufacturing at least one compound of formula (II) from at least one compound of formula (I): $CX(Y)_2$—$CX(Y)_m$—$CH_mXY$ in which X and Y independently represent a hydrogen, fluorine or chlorine atom and m=0 or 1.

The process according to the present invention comprises at least one step during which at least one compound of formula (I) reacts with HF in the gaseous phase in the presence of a fluorination catalyst to give at least one compound of formula (II), characterized in that the catalyst is based on chromium oxyfluoride containing nickel as cometal and at least one rare-earth metal.

As compounds of formula (II), mention may be made especially of 2,3,3,3-tetrafluoropropene (HFO-1234yf), 1,3,3,3-tetrafluoropropene (HFO-1234ze), 1-chloro-3,3,3-trifluoro-1-propene (HCFO-1233zd), 2-chloro-3,3,3-trifluoro-1-propene (HCFO-1233xf), 1,2-dichloro-3,3,3-trifluoropropane (HCFC-243db), 2-chloro-2,3,3,3-tetrafluoropropane (HCFC-244bb), 1,1,1,2,2-pentafluoropropane (HFC-245cb), 1-chloro-1,3,3,3-tetrafluoropropane (HCFC-244fa) and 1,1,1,3,3-pentafluoropropane (HFC-245fa).

Preferably, the compounds of formula (II) are chosen from 2,3,3,3-tetrafluoropropene (HFO-1234yf), 1,3,3,3-tetrafluoropropene (HFO-1234ze) and 1-chloro-3,3,3-trifluoro-1-propene (HCFO-1233zd).

As compounds of formula (I), mention may be made especially of tetrachloropropenes, in particular 1,1,2,3-tetrachloropropene (HCO-1230xa), 2,3,3,3-tetrachloropropene (HCO-1230xf), 1,1,3,3-tetrachloropropene (HCO-1230za) and 1,3,3,3-tetrachloropropene (HCO-1230zd), and pentachloropropanes, in particular 1,1,1,2,3-pentachloropropane (HCC-240db), 1,1,1,3,3-pentachloropropane (HCC-240fa) and 1,1,2,2,3-pentachloropropane (HCC-240aa).

According to one embodiment of the present invention, 2,3,3,3-tetrafluoropropene is manufactured from halopropanes of formulae $CX_3CHClCH_2X$ and $CX_3CFXCH_3$, and halopropenes of formulae $CX_3CCl=CH_2$, $CClX_2CCl=CH_2$ and $CX_2=CClCH_2X$, with X independently representing a fluorine or chlorine atom.

Preferably, 2,3,3,3-tetrafluoropropene is manufactured from 1,1,1,2,3-pentachloropropane, 1,1,2,3,tetrachloropropene, 1,2-dichloro-3,3,3-trifluoropropane, 1,1,1,2,2-pentafluoropropane and/or 2-chloro-3,3,3-trifluoro-1-propene.

According to this embodiment, 2,3,3,3-tetrafluoropropene is advantageously manufactured from 1,1,1,2,3-pentachloropropane and/or 2-chloro-3,3,3-trifluoro-1-propene.

According to another embodiment of the present invention, 1,3,3,3-tetrafluoropropene is manufactured from 1,1,1,3,3-pentachloropropane, 1,1,3,3-tetrachloropropene, 1,1-dichloro-3,3,3-trifluoropropane, 1,1,1,3,3-pentafluoropropane and/or 1-chloro-3,3,3-trifluoro-1-propene.

According to this embodiment, 1,3,3,3-tetrafluoropropene is preferably manufactured from 1,1,1,3,3-pentachloropropane and/or 1-chloro-3,3,3-trifluoro-1-propene.

According to another embodiment of the present invention, 1-chloro-3,3,3-trifluoro-1-propene, in particular the trans isomer, is manufactured from 1,1,1,3,3-pentachloropropane and/or 1,1,3,3-tetrachloropropene.

As rare-earth metal included in the composition of the catalyst used in the process according to the present invention, mention may be made especially of lanthanum, cerium, praseodymium, neodymium, promethium, samarium, europium, gadolinium, terbium, dysprosium, holmium, erbium, thulium, ytterbium, lutetium, yttrium and scandium.

Recycled rare-earth metals may be suitable for use in the preparation of the catalyst.

The preferred rare-earth metals are cerium, lanthanum and praseodymium.

The atomic ratio of rare-earth metal(s)/chromium in the catalyst is preferably between 0.001-0.1 and advantageously between 0.001-0.02.

The atomic ratio of nickel cometal/chromium in the catalyst is preferably between 0.5 and 5 and advantageously between 0.7 and 2.

Irrespective of the embodiment of the invention, the temperature of the fluorination step may be between 100 and 500° C., preferably between 180 and 420° C. and advantageously between 280 and 420° C. The mole ratio of HF relative to the total amount of compounds of formula (I) to be reacted is preferably between 5 and 40 and advantageously between 10 and 25.

Irrespective of the embodiment, the fluorination step may be performed in the presence of an oxidizing agent with a mole ratio of oxidizing agent relative to the compound(s) of formula (I) preferably between 0.005 and 2.

The fluorination step is generally performed at a pressure of between 0.1 and 20 bar, preferably between 1 and 7 bar.

The oxidizing agent may be chosen from oxygen, chlorine and air.

The catalyst used may be in bulk or supported form.

As catalyst support, mention may be made especially of charcoal or magnesium derivatives, especially halides such as $MgF_2$ or magnesium oxyhalides such as alumina oxyfluorides, which are optionally activated, or aluminum derivatives, especially halides, such as $AlF_3$ or aluminum oxyhalides such as oxyfluoride.

The catalyst used in the present invention may be prepared by coprecipitation of the corresponding salts based on chromium, nickel and rare-earth metals optionally in the presence of a support.

The catalyst may also be prepared by comilling of the corresponding oxides. Prior to the fluorination reaction, the catalyst is subjected to a step of activation with HF.

The HF treatment temperature may be between 100 and 450° C., preferably between 200 and 300° C., for a time of between 1 and 50 hours.

According to another embodiment, the activation of the catalysts may be performed in at least one step with a treatment using a mixture of HF and of oxidizing agent. The oxidizing agent may represent between 2 mol % and 98 mol % relative to the mixture of HF and of oxidizing agent and the activation temperature may range between 200 and 450° C. for a time of between 10 and 200 hours.

The activation steps may be performed at atmospheric pressure or at a pressure of up to 20 bar.

The support may be prepared using highly porous alumina. In a first step, the alumina is converted into aluminum fluoride or into a mixture of aluminum fluoride and alumina, by fluorination using air and hydrofluoric acid, the degree of conversion of the alumina into aluminum fluoride depending essentially on the temperature at which the fluorination of the alumina is performed (in general between 200° C. and 450° C., preferably between 250° C. and 400° C.). The support is then impregnated using aqueous solutions of chromium, nickel and rare-earth metal salts, or using aqueous solutions of chromic acid, of nickel salt and of rare-earth metal salts or oxides and methanol (serving as chromium reducer). As chromium, nickel and rare-earth metal salts, use may be made of chlorides, or of other salts, for instance nickel and rare-earth metal oxalates, formates, acetates, nitrates and sulfates or dichromate, provided that these salts are soluble in the amount of water capable of being absorbed by the support.

The catalyst may also be prepared by direct impregnation of alumina (which is generally activated) using solutions of the chromium, nickel and rare-earth metal compounds mentioned above. In this case, the conversion of at least part (for example 70% or more) of the alumina into aluminum fluoride or aluminum oxyfluoride is performed during the step of activation of the metal of the catalyst.

The activated aluminas that may be used for the preparation of the catalyst are products that are well known, which are commercially available. They are generally prepared by calcination of alumina hydrates (aluminum hydroxides) at a temperature of between 300° C. and 800° C. The aluminas (activated or not activated) may contain large amounts (up to 1000 ppm) of sodium without this harming the catalytic performance.

Preferably, the catalyst is conditioned or activated, i.e. converted into constituents that are active and stable (under the reaction conditions) via a preactivation operation. This treatment may be performed either "in situ" (in the fluorination reactor) or in suitable apparatus designed to withstand the activation conditions.

After impregnation of the support, the catalyst is dried at a temperature of between 100° C. and 350° C., preferably 220° C. to 280° C., in the presence of air or nitrogen.

The dried catalyst is then activated in one or two steps with hydrofluoric acid, optionally in the presence of an oxidizing agent. The duration of this step of activation by fluorination may be between 6 and 100 hours and the temperature may be between 300 and 400° C.

The process according to the present invention may be performed continuously or in batch mode.

The present invention also provides a process for isomerization or dehydrohalogenation in the presence of the catalyst as described above.

As examples of isomerizations, mention may be made especially of the production of 2,3,3,3-tetrafluoropropene from 1,3,3,3-tetrafluoropropene and the reverse reaction, the production of 2-chloro-3,3,3-trifluoro-1-propene from 1-chloro-3,3,3-trifluoro-1-propene and the reverse reaction, the production of the trans isomer of 1-chloro-3,3,3-trifluoro-1-propene from the cis isomer and the production of the trans isomer of 1,3,3,3-tetrafluoropropene from the cis isomer.

As examples of dehydrohalogenations, mention may be made especially of the production of 2,3,3,3-tetrafluoropropene from 2-chloro-2,3,3,3-tetrafluoropropane and/or 1,1,1,2,2-pentafluoropropane and the production of 1,3,3,3-tetrafluoropropene from 1-chloro-1,3,3,3-tetrafluoropropane and/or 1,1,1,3,3-pentafluoropropane.

As compounds of formula (I), mention may also be made of 1,2-dichloro-3,3,3-trifluoropropane, 2-chloro-2,3,3,3-tetrafluoropropane, 1,1,1,2,2-pentafluoropropane, 1-chloro-1,3,3,3-tetrafluoropropane and 1,1,1,3,3-pentafluoroprapane.

EXPERIMENTAL SECTION

The apparatus used comprises a tubular reactor made of Inconel® 600 with an inside diameter of 19 mm, heated by a tubular oven. The reactor is equipped with pressure and temperature regulators. The reagents are preheated and mixed, by means of a static mixer, and then introduced in the gaseous phase into the upper part of the reactor.

On exiting the reactor, a sample of the reaction products is taken and is analyzed online by gas chromatography. The analysis is performed using a CP Sil 8CB column, of dimensions 50 m×0.32 mm×5 µm, and a 1% SP1000/Carbopack B, 60/80 mesh packed column 5 m long. The oven temperature programs are as follows: 40° C. for 10 min then ramp of 10° C./min upto 250° C. and 40° C. for 20 min then ramp of 10° C./min to 180° C.

The contact time is defined as the ratio of the volume of the catalytic bed to the total volume flow rate under the temperature and pressure experimental conditions. The HF mole ratio is defined as the ratio between the molar flow rate of HF and the molar flow rate of HCFO-1233xf. The reaction is performed in the presence of air. The oxygen mole ratio is defined as the ratio between the molar flow rate of oxygen and the molar flow rate of HCFO-1233xf.

Example 1: Fluorination of HCFO-1233xf

The catalyst used is an Ni—Cr/AlF$_3$ catalyst prepared as follows.

343 g of a support obtained in a preceding step by fluorination of GRACE HSA alumina in a fixed bed at about 280° C. using air and hydrofluoric acid (volume concentration of 5% to 10% of this acid in the air) are placed in a rotary evaporator. The starting GRACE HSA alumina has the following physicochemical characteristics: beads 0.5-2 mm in diameter with a BET surface area=220 m$^2$/g, pore volume=1.3 cm$^3$/g.

Two separate aqueous solutions are moreover prepared:
(a) chromic solution supplemented with nickel chloride containing:
chromium trioxide CrO$_3$=55 g
nickel chloride hexahydrate NiCl$_2$.6H$_2$O=130 g
water=63 g
(b) methanolic solution containing:
methanol=81 g
water=8 g These two solutions are introduced simultaneously at a temperature of 40° C. at atmospheric pressure and over about 2 hours, onto the support with stirring. After a step of maturation under nitrogen, the catalyst is dried under nitrogen, and then under vacuum at 65° C. and then at about 90° C. for 6 hours.

The fluorination of HCFO-1233xf is performed in the reactor described above by introducing 73 cm$^3$ of Ni—Cr catalyst supported on AlF$_3$.

After the introduction, the solid is treated at a temperature of between 320° C. and 390° C. in the presence of a mixture of hydrofluoric acid and nitrogen (volume concentration of 5% to 10% of this acid in the nitrogen).

The activation process then comprises 5 cycles of:
fluorination of the catalyst by performing the fluorination reaction for 6 to 30 hours under the conditions stated below,
treatment in air at 370° C. and 1.5 L/h for 64 hours.

The reaction is performed by continuously feeding in 3.4 g/h of anhydrous HF and 1.0 g/h of HCFO-1233xf at atmospheric pressure and at a temperature of 350° C. Thus, the contact time is 29 s, the HF mole ratio is 22. The amount of oxygen is 8 mol % relative to the amount of HCFO-1233xf.

The results are presented in the table below.

Comparative Example 2: Fluorination of HCFO-1233xf

The catalyst used is an Ni—Cr—La/AlF$_3$ catalyst prepared as previously, the chromic solution supplemented with nickel chloride and lanthanum chloride containing:
chromium trioxide CrO$_3$=55 g
nickel chloride hexahydrate NiCl$_2$.6H$_2$O=130 g
lanthanum chloride hexahydrate LaCl$_3$.6H$_2$O=2 g
water=63 g The fluorination of HCFO-1233xf is performed in the reactor described above by introducing 73 cm$^3$ of Ni—Cr—La catalyst supported on AlF$_3$.

The activation process is identical and the reaction is also performed by continuously feeding in 3.4 g/h of anhydrous HF and 1.0 g/h of HCFO-1233xf at atmospheric pressure and at a temperature of 350° C. The amount of oxygen is 8 mol % relative to the amount of HCFO-1233xf.

The full results are presented in the table below.

|  | Reaction time | Conversion (%) | Selectivity toward HFO-1234yf | Selectivity toward HFC-245cb | Selectivity toward others |
|---|---|---|---|---|---|
| Example 1 | 7 h | 69.7% | 65.7% | 32.8% | 1.5% |
|  | 33 h | 54.7% | 64.6% | 32.3% | 3.1% |
| Example 2 | 8 h | 70.2% | 66.4% | 32.4% | 1.2% |
|  | 41 h | 63.8% | 65.1% | 32.6% | 2.3% |

The invention claimed is:

1. A process for manufacturing at least one compound of formula (II): CF$_3$—CX(Z)$_n$—CHX(Z)$_n$ in which X independently represents a hydrogen, fluorine or chlorine atom, Z independently represents a hydrogen or fluorine atom and n=0 or 1, comprising at least one step during which at least one compound of formula (I): CX(Y)$_2$—CX(Y)$_m$—CH$_m$XY in which X and Y independently represent a hydrogen, fluorine or chlorine atom and m=0 or 1, reacts with HF in the gaseous phase in the presence of a fluorination catalyst, characterized in that the catalyst is based on chromium oxyfluoride containing at least nickel as co-metal and at least one rare-earth metal.

2. The process as claimed in claim 1, characterized in that the compounds of formula (II) are chosen from 2,3,3,3-tetrafluoropropene, 1,3,3,3-tetrafluoropropene, 1-chloro-3,3,3-trifluoro-1-propene, and 2-chloro-3,3,3-trifluoro-1-propene.

3. The process as claimed in claim 1, characterized in that the compounds of formula (I) are chosen from 1,1,2,3-tetrachloropropene, 2,3,3,3-tetrachloropropene, 1,1,3,3-tetrachloropropene, 1,3,3,3-tetrachloropropene, 1,1,1,2,3-pentachloropropane, 1,1,1,3,3-pentachloropropane, 1,1,2,2,3-pentachloropropane, 1,2-dichloro-3,3,3-trifluoropropane, 2-chloro-2,3,3,3-tetrafluoropropane, 1,1,1,2,2-pentafluoropropane, 1-chloro-1,3,3,3-tetrafluoropropane and 1,1,1,3,3-pentafluoropropane.

4. The process as claimed in claim 1, characterized in that 2,3,3,3-tetrafluoropropene is manufactured from halopropanes of formulae CX$_3$CHClCH$_2$X and CX$_3$CFXCH$_3$, halopropenes of formulae CX$_3$CCl═CH$_2$, CClX$_2$CCl═CH$_2$ and CX$_2$═CClCH$_2$X, with X independently representing a fluorine or chlorine atom.

5. The process as claimed in claim 1, characterized in that 2,3,3,3-tetrafluoropropene is manufactured from 1,1,1,2,3-pentachloropropane, 1,1,2,3-tetrachloropropene, 1,1,1,2,2-pentafluoropropane and/or 2-chloro-3,3,3-trifluoro-1-propene.

6. The process as claimed in claim 2, characterized in that 1,3,3,3-tetrafluoropropene is manufactured from 1,1,1,3,3-pentachloropropane, 1,1,3,3-tetrachloropropene, 1,1,1,3,3-pentafluoropropane and/or 1-chloro-3,3,3-trifluoro-1-propene.

7. The process as claimed in claim 2, characterized in that 1-chloro-3,3,3-trifluoro-1-propene is manufactured from 1,1,1,3,3-pentachloropropane and/or 1,1,3,3-tetrachloropropene.

8. The process as claimed in claim 1, characterized in that the rare-earth metal(s) are chosen from cerium, lanthanum and praseodymium.

9. The process as claimed in claim 1, characterized in that the atomic ratio of rare-earth metal(s)/chromium in the catalyst is between 0.001-0.1, preferably between 0.001-0.02.

10. The process as claimed in claim 1, characterized in that the nickel co-metal/chromium atomic ratio in the catalyst is between 0.5 and 5 and preferably between 0.7 and 2.

11. The process as claimed in claim 1, characterized in that the catalyst is supported.

12. The process as claimed in claim 11, characterized in that the support is chosen from charcoal, magnesium derivatives, alumina or aluminum derivatives.

13. The process as claimed in claim 1, characterized in that the mole ratio of HF relative to the compounds of formula (I) to be reacted is between 5 and 40, preferably between 10 and 25.

14. The process as claimed in claim 1, characterized in that the fluorination temperature is between 180 and 420° C., preferably between 280 and 420° C.

15. The process as claimed in claim 1, characterized in that the catalyst is subjected to at least one activation step using a stream comprising HF.

* * * * *